(12) United States Patent
Gurjar et al.

(10) Patent No.: US 8,686,165 B2
(45) Date of Patent: Apr. 1, 2014

(54) PROCESS FOR PREPARATION OF TAXANE DERIVATIVES

(75) Inventors: Mukund K. Gurjar, Pune (IN); Swapnil P. Sonawane, Pune (IN); Pankaj S. Patil, Pune (IN); Samit S. Mehta, Pune (IN)

(73) Assignee: Emcure Pharmaceuticals Limited, Pune (IN)

( * ) Notice: Subject to any disclaimer, the term of this patent is extended or adjusted under 35 U.S.C. 154(b) by 220 days.

(21) Appl. No.: 12/917,823

(22) Filed: Nov. 2, 2010

(65) Prior Publication Data

US 2011/0105598 A1    May 5, 2011

(30) Foreign Application Priority Data

Nov. 4, 2009    (IN) .......................... 2559/MUM/2009

(51) Int. Cl.
*C07D 305/14*    (2006.01)
*C07D 305/06*    (2006.01)

(52) U.S. Cl.
USPC .......................................... 549/510; 549/511

(58) Field of Classification Search
USPC .................................................. 549/510, 511
See application file for complete search history.

(56) References Cited

U.S. PATENT DOCUMENTS

| 6,022,985 | A | 2/2000 | Authelin et al. |
| 6,197,980 | B1 | 3/2001 | Durand et al. |
| 6,838,569 | B2 | 1/2005 | Sharma et al. |
| 7,332,617 | B2 | 2/2008 | Li et al. |
| 7,662,980 | B2 * | 2/2010 | Liao et al. ...................... 549/510 |
| 8,133,888 | B2 * | 3/2012 | Patel et al. .................. 514/232.8 |
| 8,163,940 | B2 * | 4/2012 | Pyo et al. ...................... 549/510 |
| 8,207,358 | B2 * | 6/2012 | Lourdusamy et al. ........ 549/510 |
| 8,263,793 | B2 * | 9/2012 | Caron et al. ................... 549/510 |
| 2009/0221688 | A1 | 9/2009 | Machado et al. |

* cited by examiner

*Primary Examiner* — Andrew D Kosar
*Assistant Examiner* — Raymond Covington
(74) *Attorney, Agent, or Firm* — Blank Rome LLP

(57) ABSTRACT

The present disclosure relates to processes for the preparation of taxane derivatives with improved purity and enhanced stability. The taxane derivatives prepared according to the processes described herein are useful for the preparation of pharmaceutical compositions.

28 Claims, No Drawings

PROCESS FOR PREPARATION OF TAXANE DERIVATIVES

This application claims the benefit of Indian Patent Application No. 2559/MUM/2009, filed on Nov. 4, 2009, which is hereby incorporated by reference.

FIELD OF THE INVENTION

The present invention relates to an improved process for the preparation of taxane derivatives. More particularly, this invention relates to a novel method for minimizing the levels of the impurities, such as the epi-isomer at the 7-position of baccatin ring (the principal degradation product), formed during synthesis and/or storage of the taxane derivative.

BACKGROUND OF THE INVENTION

Because of their novel molecular architecture, potent biological activity and fascinating mode of action, the taxane derivatives paclitaxel (I) and docetaxel (II) have become the mainstay in cancer chemotherapy.

|  | R' | R |
| --- | --- | --- |
| Paclitaxel (I) | Ac | —C(O)—Ph |
| Docetaxel (II) | H | —C(O)—OBu-t |

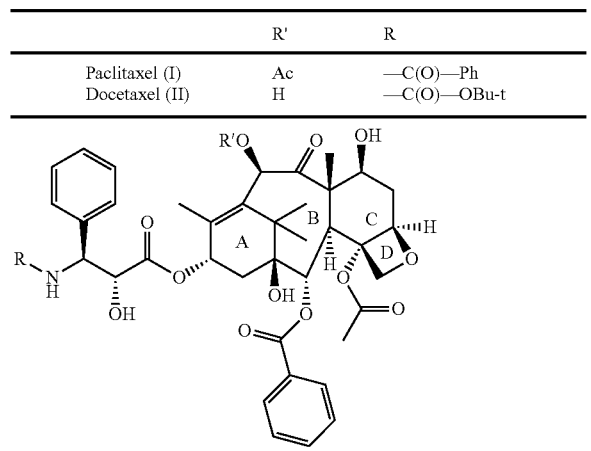

Currently, paclitaxel, which is marketed under the brand name Taxol®, is approved in the U.S. for (i) first-line (in combination with cisplatin) and subsequent therapy for the treatment of advanced carcinoma of the ovary, (ii) the adjuvant treatment of node-positive breast cancer when administered sequentially to standard doxorubicin-containing combination chemotherapy, (iii) the treatment of breast cancer after failure of chemotherapy for metastatic disease or within 6 months of adjuvant chemotherapy, (iv) the first-line treatment of non-small cell lung cancer in patients who are not candidates for potentially curative and/or radiation therapy (in combination with cisplatin) and (v) the second-line treatment of AIDS-related Kaposi's carcinoma.

Docetaxel (Taxotere®) is approved in the U.S. for (i) the treatment of patients with locally advanced or metastatic breast cancer after failure of chemotherapy, (ii) the adjuvant treatment of patients with operable node-positive breast cancer (in combination with doxorubicin and cyclophosphamide), (iii) the treatment of patients with locally advanced or metastatic non-small cell lung cancer after failure of prior platinum-based chemotherapy, (iv) the treatment of patients with unresectable locally advanced or metastatic non-small cell lung cancer who have not previously received chemotherapy (in combination with cisplatin), (v) the treatment of patients with androgen independent (hormone refractory) metastatic prostate cancer (in combination with prednisone), (vi) the treatment of patients with advanced gastric adenocarcinoma, including carcinoma of the gastroesophageal junction, who have not received prior chemotherapy for advanced disease (in combination with cisplatin and fluorouracil), and (vii) the induction treatment of patients with locally advanced squamous cell carcinoma of the head and neck (in combination with cisplatin and fluouracil).

Paclitaxel is found in several species of yew (genus *Taxus*, family Taxaceae) trees; however, the concentration of this compound is very low. Paclitaxel, docetaxel and their analogues, such as cabazitaxel, are built upon the baccatin III framework. Since the safety and efficacy of paclitaxel and docetaxel are proven, these compounds continue to stimulate synthetic chemists for further refinement of chemical development process. However, these taxane derivatives present a plethora of potential problems related to their synthesis and pharmaceutical compositions containing them, primarily due to stability problems.

Docetaxel is marketed worldwide in its trihydrate form and was first disclosed in U.S. Pat. No. 6,197,980. U.S. Pat. No. 6,022,985 discloses that the trihydrate form has a substantially greater stability than that of the anhydrous form. U.S. Pat. No. 6,022,985 further discloses that trihydrate docetaxel is stable at 4° C., 25° C. and 35° C. in an atmosphere with 90% relative humidity up to 18 months without any danger to its hydrated form whereas the anhydrous form has a tendency to slowly change to the trihydrate form. Further, U.S. Pat. No. 6,022,985 also discloses that it may be advantageous to perform the crystallization in the presence of an acid such as ascorbic acid. However, there is no data in support of any advantageous effect obtained by addition of an acid during crystallization.

Recently, due to the enhanced stability of the trihydrate form of this taxane derivative, there has been an increasing interest in the methods for preparation of taxanes, especially docetaxel in trihydrate form.

U.S. Pat. No. 6,838,569 discloses a process for the preparation of docetaxel and paclitaxel trihydrate using acetonitrile and water. However, again there is no mention of any stability data of docetaxel obtained by such a process. Similarly, U.S. Pat. No. 7,332,617 discloses that docetaxel trihydrate can be prepared by using an acetone/water combination.

It should be noted, however, that the anhydrous as well as the relatively more stable trihydrate form of taxane are liable to undergo degradation, at times drastic, under various manufacturing and storage conditions (for example, temperature, acidic and alkaline media, light, etc.) One of the probable and possibly the most prone pathway for degradation normally observed is epimerization of the hydroxyl group at position 7, which results in formation of the 7-epi-isomer by way of a retro aldol reaction. The epimerization reaction has been observed in alkaline, neutral, and strongly acidic media. Further, in acidic media, or in the presence of electrophilic agents, opening and/or rearrangements of ring D as well as ring B are prominent, whereas in basic media cleavage of the ester groups at positions 2, 4 and/or 13 is observed. It is also reported that 10-deacetyl baccatin III, which is normally employed as a starting material for synthesis of docetaxel, and its epimer (7-epi-10-deacetyl baccatin III) are formed in basic conditions. See, e.g., U.S. Publication No. 2009/0221688, which is hereby incorporated by reference. Basic conditions also lead to formation of 7-epi-10-oxo-10-deacetyl baccatin III. Of these major degradation products of docetaxel, the formation of 7-epi-docetaxel by way of a retro aldol reaction has vexed researchers in this field because 7-epi-docetaxel is thermodynamically more stable and hence its formation is favored. The probable mechanism for formation of 7-epimer of taxane derivative is summarized in Scheme 1.

Scheme - 1: Probable mechanism for formation of 7-epi derivative from taxane derivetives

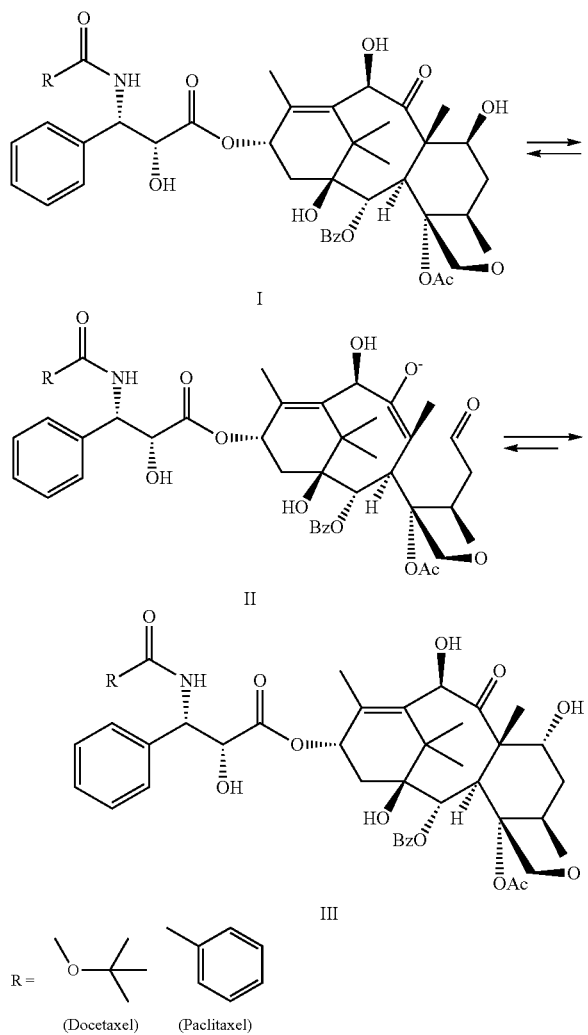

The degradation of taxane derivatives can result in products with reduced desired pharmacological activity or at times may result in completely inactive products or products with completely different pharmacological and toxicological pattern. Moreover, health authorities all over the world have very stringent requirements for permissible limits of these degradation products in the final formulation.

Hence, there is a need for new synthetic processes which minimize the formation of impurities during the synthesis reaction as well as on storage of taxane derivatives.

OBJECTS OF THE INVENTION

An object of the present invention is to provide a taxane derivative which has minimum impurities resulting from degradation.

Another object of the present invention is to provide a taxane derivative which is more stable for a pharmaceutically acceptable duration time.

Still another object of the present invention is to provide a process for minimization of impurities formed in a taxane derivative during synthesis or on storage.

A further object of the present invention is to provide a pharmaceutical composition prepared by using a taxane derivative with minimum degradation impurities.

Yet further another object of the present invention is to provide a method to reduce the formation of a thermodynamically stable epimerization product, such as 7-epi-docetaxel or 7-epi-paclitaxel, formed during the synthesis of docetaxel and paclitaxel, respectively.

SUMMARY OF THE INVENTION

The present inventors have surprisingly found that degradation of a taxane derivative may be minimized by carrying out isolation of the taxane derivative from reaction mixtures in the presence of one or more metal salts. When isolation of a taxane derivative is performed in the presence of a metal salt, the resulting taxane derivative product not only may be isolated in a purer form, but the product also exhibits enhanced storage stability.

Thus, the present invention provides a process for synthesis of a taxane derivative, such as paclitaxel, docetaxel and cabazitaxel, either in anhydrous form or in hydrated form, wherein the degradation of the active principal (to form the 7-epimer impurity) is reduced. Thus, the process results in a taxane derivative of high purity. Moreover, the taxane derivative obtained by such a process has enhanced stability during storage, rendering it highly suitable for commercial purposes.

The present invention provides a process for the synthesis of a taxane derivative, wherein the product obtained by such a process withstands the higher temperatures generated during the manufacturing of a pharmaceutical composition.

In one embodiment, the present invention relates to a process for the preparation of a taxane derivative that involves the step of isolating the taxane derivative in the presence of a metal salt.

In another embodiment, the present invention relates to a process for reducing the formation of impurities, such as the 7-epimer impurity, during synthesis of a taxane derivative, the process involving the step of isolating the taxane derivative in the presence of a metal salt.

In another embodiment, the present invention relates to a taxane derivative prepared by a process that involves the step of isolating the taxane derivative in the presence of a metal salt. For instance, the taxane derivative can be isolated from an aqueous mixture containing a metal salt and one or more organic solvents.

The taxane derivative can be purified, for example, by (i) providing a mixture of the taxane derivative with a metal salt (such as aluminum sulfate, potassium aluminum sulfate, or a mixture thereof) in water and one or more organic solvents (such as ethanol, cyclohexane, ethyl acetate, or any combination of any of the foregoing), and (ii) concentrating the mixture. Preferably, the taxane derivative is dissolved in the aqueous mixture and one or more organic solvents.

In another embodiment, the present invention relates to a pharmaceutical composition that contains a taxane derivative prepared by a process that involves the step of isolating the taxane derivative in the presence of a metal salt, and a pharmaceutically acceptable carrier.

DETAILED DESCRIPTION OF THE INVENTION

The present invention relates to a method for reducing degradation impurities formed either during the synthesis of a taxane derivative, or during storage of the taxane derivative. Thus, taxane derivatives obtained by the processes described herein have increased purity and exhibit greater storage stability, e.g., when stored for a pharmaceutically acceptable duration of time. The present methods may be employed to prepare substantially pure anhydrous taxane derivatives as well as substantially pure trihydrate taxane derivatives.

As used herein the term "substantially pure" means a taxane derivative having degradation impurities less than about 1% and an amount of 7-epimerized product less than about 0.2%, for example, even after storage at room temperature for a pharmaceutically acceptable duration of time.

As used herein, the term "pharmaceutically acceptable duration of time" means a duration of time, generally known in the art, during which a composition containing a taxane derivative remains suitable for use as a pharmaceutical. For example, a pharmaceutically acceptable duration of time may be up to 2 years at room temperature or may be a period of up to 2 years at between 2° C. and 25° C.

The present inventors, while attempting to prepare taxane derivatives using known methods, observed that such taxane derivatives rapidly undergo retro aldol reaction, thereby generating the 7-epimerized isomer as a major degradation product, rendering the taxane derivative less suitable for pharmaceutical use.

The present inventors have surprisingly found that degradation of the taxane derivative may be minimized by isolating the taxane derivative from a reaction mixture in the presence of one or more metal salts. When isolation of a taxane derivative, either anhydrous or in its trihydrate form, is performed in the presence of a metal salt, the resulting taxane derivative product not only may be isolated in a substantially pure form, but the product also exhibits enhanced storage stability. The present inventors have observed, e.g., almost a 10-fold reduction in formation of the epimerized product when a taxane derivative (e.g., docetaxel) is isolated in the presence of a metal salt, when compared to a taxane derivative that is not isolated in the presence of a metal salt.

Thus, in one aspect, the present invention relates to a process for the preparation of a taxane derivative that involves the step of isolating the taxane derivative in the presence of a metal salt.

As used herein, the term "metal salt" means any molecule having the general formula $[M^{q+}]_a[X^{z-}]_b$ wherein X is any negatively charged ion, a, b, q and z are independently integers $\geq 1$, q(a)=z(b). The metals salts may be organic or inorganic metal salts. Inorganic metal salts are preferred. Metal salts that are highly soluble in water are particularly preferred.

Suitable example of metal salts include inorganic metal salts such as, but not limited to, aluminum sulfate, potassium aluminum sulfate, lithium dihydrogen phosphate, sodium dihydrogen phosphate, potassium trisulfite, potassium hydrogen sulfate, potassium dihydrogen phosphate, sodium hydrogen sulfite, calcium aluminium sulfate. Preferred metal salts include aluminum sulfate and potassium aluminum sulfate.

The metal salt can be added in a concentration from about 1.0% to about 10% by weight of taxane derivative. Preferably, the metal salt is added in a concentration in the range of about 1.5 to about 4.0%, and more preferably in the range of about 2.0 to about 3.0% by weight of taxane derivative.

Any synthetic route known in the art may be employed for the synthesis of the anhydrous as well as the trihydrate form of the taxane derivative. The present inventors have found that the stability of the final taxane product is not particularly dependent on the synthetic route employed, as long as isolation of the taxane derivative is carried out in the presence of metal salt according to the processes of the present invention. Thus, the use of a metal salt during isolation of taxane derivative, according the processes of the present invention, affords a manufacturer the freedom to choose the solvents, reagents, reaction conditions and other parameters.

In another aspect, the present invention relates to a process for reducing the formation of impurities, such as the 7-epimer impurity, during synthesis of a taxane derivative, the process involving the step of isolating the taxane derivative in the presence of a metal.

In another aspect, the present invention relates to a taxane derivative, prepared by any of the processes of the present invention described herein.

In another aspect, the present invention relates to a pharmaceutical composition that contains a taxane derivative, prepared by any of the processes of the present invention described herein, and a pharmaceutically acceptable excipient.

Suitable excipients include, for example, emulsifiers, stabilizers, sweeteners, flavoring agents, diluents, coloring agents and/or solubilizing agents, and the like, or any combination thereof. Suitable excipients, emulsifiers, stabilizers, sweeteners, flavoring agents, diluents, coloring agents, and solubilizing agents include those described in the *Handbook of Pharmaceutical Excipients* (fourth edition) by Raymond C. Rowe, Paul J. Sheskey and Paul J. Weller.

The pharmaceutical composition may be, for example, an injectable solution. Suitable injectable solutions may include, for example, ethanol, water, saline solution and/or sugar solution (e.g., dextrose solution).

In further embodiments, a pharmaceutical composition that contains a taxane derivative, prepared by any of the processes of the present invention described herein, may also contain a polysorbate (e.g., polysorbate 80), a cremophore, an alcohol, and combinations thereof.

The principles, preferred embodiments, and modes of operation of the present invention have been described in the foregoing specification. The invention which is intended to be protected herein, however, is not to be construed limited to the particular forms disclosed, since these are to be regarded as illustrative rather than restrictive. Variations and changes may be made by those skilled in the art, without departing from the spirit of the invention.

The invention is further explained with the help of following illustrative examples, however, in no way these examples should be construed as limiting the scope of the invention.

EXAMPLES

Example 1

Preparation of Docetaxel Trihydrate

4-Acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate (30 g) was purified using silica gel flash chromatography utilizing a mixture of dichloromethane:methanol in appropriate concentration for elution. The fraction containing the desired product was concentrated under reduced pressure to give a syrupy mass, which was dissolved in a mixture of ethanol:cyclohexane:demineralised water:ethyl acetate (20:2:10:0.8) containing 0.02 g aluminum sulfate at 25-30° C. under constant stirring. The clear biphasic reaction was then concentrated to 20 ml and cooled to 5-10° C. The precipitated solid was stirred for 25-30 minutes at 5-10° C., then filtered, washed with demineralised water (1 ml) and dried under reduced pressure under a humid atmosphere (until the moisture content was between 5-7% by Karl Fischer method) to afford Docetaxel trihydrate in 70-90% yield.

Example 2

Preparation of Docetaxel Trihydrate

Crude docetaxel (1.0 g) was dissolved in a mixture of ethanol:cyclohexane:demineralised water:ethyl acetate (20:2:10:0.8) containing 0.02 g potassium aluminum sulfate at 25-30° C. under constant stirring. The clear biphasic reaction was then concentrated to 20 ml and cooled to 5-10° C. The precipitated solid was stirred for 25-30 minutes at 5-10° C., then filtered, washed with demineralised water (1 ml) and dried under vacuum under a humid atmosphere (until the moisture content was between 5-7% by Karl Fischer method) to afford Docetaxel trihydrate in 70-90% yield.

Example 3

Preparation of Docetaxel Trihydrate

Crude docetaxel (1.0 g,) was dissolved in 1,4-dioxane (5 ml) at 25-30° C. under constant stirring. Demineralised water (7 ml) containing 0.02 g of potassium aluminum sulfate was added slowly at 25-30° C. with constant stirring. The precipitated solid was stirred for 25-30 minutes at 25-30° C., then filtered, washed with a 1:1 solution of 1,4-dioxane and demineralised water (1 ml), dried under vacuum under humid atmosphere (until the moisture content was between 5-7% by Karl Fischer method) to afford Docetaxel trihydrate in 70-90% yield Example 4

Preparation of Paclitaxel

Crude paclitaxel (1.0 g) was dissolved in a mixture of ethanol:cyclohexane:demineralised water:ethyl acetate (20:2:10:0.8) containing 0.02 g aluminum sulfate at 25-30° C. under constant stirring. The clear biphasic reaction was then concentrated to 20 ml and cooled to 5-10° C. The precipitated solid was stirred for 25-30 min. at 5-10° C., then filtered, washed with a 1:1 mixture of demineralised water:ethanol (1 ml) and dried under vacuum to afford Paclitaxel in 70-90% yield.

Example 5

Preparation of Paclitaxel

Crude paclitaxel (1.0 g) was dissolved in a mixture of ethanol:cyclohexane:demineralised water:ethyl acetate (20:2:10:0.8) containing 0.02 g potassium aluminum sulfate at 25-30° C. under constant stirring. The clear biphasic reaction was then concentrated to 20 ml and cooled to 5-10° C. The precipitated solid was stirred for 25-30 min. at 5-10° C., then filtered and washed with a 1:1 mixture of DM water:Ethanol (1 ml) and dried under reduced pressure to afford paclitaxel in 70-90% yield.

Example 6

Preparation of Docetaxel Trihydrate (Comparative Example)

Crude docetaxel (1.0 g,) was dissolved in a solution of ethanol:cyclohexane:demineralised water:ethyl acetate (20:2:10:0.8) at 25-30° C. under constant stirring. The clear biphasic reaction was then concentrated to 20 ml and cooled to 5-10° C. The precipitated solid was stirred for 25-30 min. at 5-10° C., then filtered, washed with DM water (1 ml) and dried under vacuum under humid atmosphere (until the moisture content was between 5-7% by Karl Fischer method) to afford Docetaxel trihydrate in 70-90% yield.

Stability Studies

Example 7

Table 1 shows the effect of addition of aluminum sulfate on the formation of 7-epi-docetaxel, the principal degradation product of docetaxel.

TABLE 1

Comparative stability profile of docetaxel in solution at 35° C. with and without Aluminum sulphate

| Product | Without aluminum sulfate (Example 6) | | | | With aluminum sulfate (Example 1) | | | |
|---|---|---|---|---|---|---|---|---|
| | Initial | 30 min | 60 min | 360 min | Initial | 30 min | 60 min | 360 min |
| Docetaxel | 99.68% | 99.51% | 98.95% | 98.81% | 99.68% | 99.62% | 99.50% | 99.38 |
| Epi-Docetaxel | 0.11% | 0.23% | 0.34% | 0.86% | 0.11% | 0.11% | 0.12% | 0.19% |

As can be seen from Table 1, a solution of docetaxel, prepared according to a process of the present invention (using aluminum sulfate during the isolation process), shows almost a five-fold reduction in formation of the epi-isomer degradation product compared to a solution prepared without addition of a metal salt. The docetaxel solution prepared according to present invention had 0.19% of epi-docetaxel after 6 hours. In contrast, the docetaxel solution prepared without using aluminum sulfate during the isolation process showed 0.86% of epi-docetaxel after 6 hours.

Example 7

Table 2 shows two month stability data for docetaxel prepared with and without using potassium aluminum sulfate during the isolation process.

TABLE 2

Comparative stability profile of docetaxel with and without Potassium Aluminum sulphate

| Related substances by HPLC at 25 ± 2° C./60 ± 5% RH | With potassium aluminum sulfate (Example 2) | | | Without potassium aluminum sulfate |
|---|---|---|---|---|
| | Initial | 1 Month | 2 Month | 1 Month |
| 10-Deacetyl baccatin III | ND | 0.01% | 0.01% | 0.07% |
| 7-Epi-10-deacetyl baccatin III | ND | ND | ND | 0.08% |
| 7-Epi-10-oxo-10-deacetyl baccatin III | ND | ND | ND | 0.01% |
| 7-Epi-docetaxel | 0.02% | 0.022% | 0.044% | 0.18% |
| 7-Epi-10-oxo-Docetaxel | ND | ND | ND | 0.01% |
| Any individual unspecified unidentified impurity | 0.07% | 0.076% | 0.083% | 0.07% |
| Total impurities | 0.25% | 0.27% | 0.27% | 0.58% |

ND—not detected

As can be seen from Table 2, docetaxel preparing by a process of the present invention (using potassium aluminum sulfate during the isolation step) exhibited 0.27% total impurities after 1 month storage at 25±2° C./60±5% RH. In contrast, docetaxel prepared without using potassium aluminum sulfate exhibited 0.58% total impurities after one month storage under the same conditions. Further, the docetaxel preparing using potassium aluminum sulfate showed no significant further degradation after 2 months storage under the same conditions.

Example 8

A composition was prepared using docetaxel isolated in the presence of potassium aluminum sulphate and polysorbate 80. A similar composition was prepared using polysorbate 80 and docetaxel which was not isolated in presence of any metal salt. The two compositions were maintained at 45° C. and 75% RH for 1-month. Table 3 shows the stability profile for each formulation.

TABLE 3

| No. | Composition | Stability (45° C. and 75% RH) | Related Substances Single Max. Unknown Impurity | (%) | Assay (%) |
|---|---|---|---|---|---|
| 1 | Prepared using Polysorbate 80 and docetaxel (not isolated in presence of any metal salt) | Initial | 0.736 | 1.99 | 100.8 |
| | | 1 Month | 1.120 | 3.75 | 88.4 |
| 2 | Prepared using Polysorbate 80 and docetaxel (isolated in presence of potassium aluminum sulfate) | Initial | 0.043 | 0.14 | 100.1 |
| | | 1 Month | 0.405 | 0.66 | 99.1 |

As can be seen from Table 3, Composition 2 (containing docetaxel that was isolated in the presence of potassium aluminum sulfate) shows significant reduction in total impurities and the single maximum unknown impurity when compared to Composition 1 (0.66% single maximum unknown impurity after 1 month at 45° C. and 75% RH for Composition 2 compared to 3.75% single maximum unknown impurity for Composition 1 under the same conditions). Further, Composition 2 showed an assay of 99.1% after 1 month. In contrast, Composition 1 showed a lower assay of 88.4% after 1 month.

The invention claimed is:

1. A process for the preparation of a taxane derivative comprising
   (a) providing a biphasic mixture comprising the taxane derivative, water, a water soluble metal salt and one or more organic solvents; and
   (b) concentrating the biphasic reaction mixture.

2. The process of claim 1, wherein the water soluble metal salt is a water soluble inorganic metal salt.

3. The process according to claim 2, wherein the water soluble metal salt is selected from the group consisting of aluminum sulfate, potassium aluminum sulfate, lithium dihydrogen phosphate, sodium dihydrogen phosphate, potassium trisulfite, potassium hydrogen sulfate, potassium dihydrogen phosphate, sodium hydrogen sulfite, calcium aluminum sulfate, and combinations thereof.

4. The process according to claim 3, wherein the water soluble metal salt is potassium aluminum sulfate.

5. The process according to claim 3, where the water soluble metal salt is aluminum sulfate.

6. The process according to claim 1, wherein the water soluble metal salt is added in a concentration of about 1 to about 10% by weight of taxane derivative.

7. The process according to claim 6, wherein the water soluble metal salt is added in a concentration of about 2 to about 3% by weight of taxane derivative.

8. The process according to claim 1, wherein the taxane derivative is selected from the group consisting of paclitaxel, docetaxel and cabazitaxel.

9. The process according to claim 8, wherein the taxane derivative is docetaxel.

10. The process according to claim 1, wherein the taxane derivative is anhydrous or a trihydrate.

11. The process according to claim 1, wherein the taxane derivative contains less than about 1% total impurities when stored at room temperature and 60% relative humidity for about one month or more.

12. The process according to claim 11, wherein the taxane derivative contains less than about 1% total impurities when stored at room temperature and 60% relative humidity for about two months.

13. The process according to claim 1, wherein the taxane derivative contains less than about 0.2% epi-isomer impurity when stored at room temperature and 60% relative humidity for about one month or more.

14. The process according to claim 12, wherein the taxane derivative contains less than about 0.2% epi-isomer impurity when stored at room temperature and 60% relative humidity for about two months.

15. A taxane derivative, prepared according to a process comprising
   (a) providing a biphasic mixture comprising a taxane derivative, water, a water soluble metal salt and one or more organic solvents; and
   (b) concentrating the biphasic reaction mixture;
   wherein the taxane derivative contains less than about 0.2% epi-isomer impurity when stored at room temperature and 60% relative humidity for about one month or more.

16. The taxane derivative of claim 15, where the taxane derivative is selected from the group consisting of paclitaxel, docetaxel and cabazitaxel.

17. A pharmaceutical composition comprising a taxane derivative according to claim 15 and a pharmaceutically acceptable carrier.

18. The pharmaceutical composition of claim 17, further comprising a polysorbate, a cremophore, an alcohol, or a combination thereof.

19. The pharmaceutical composition of claim 17, in the form of an injectable solution.

20. A process for reducing the formation of a 7-epimer impurity during synthesis of a taxane derivative comprising
   (a) providing a biphasic mixture comprising a taxane derivative, water, a water soluble metal salt and one or more organic solvents; and
   (b) concentrating the biphasic reaction mixture.

21. The process of claim 1, wherein said biphasic mixture comprises ethanol, cyclohexane, water and ethyl acetate.

22. The process of claim 21, wherein the ratio of ethanol:cyclohexane:water:ethyl acetate is about 20:2:10:0.8.

23. The process of claim 20, wherein said biphasic mixture comprises ethanol, cyclohexane, water and ethyl acetate.

24. The process of claim 23, wherein the ratio of ethanol:cyclohexane:water:ethyl acetate is about 20:2:10:0.8.

25. The process according to claim 1, wherein the concentrating step comprises isolating docetaxel or paclitaxel from the biphasic mixture.

26. The process according to claim 25, wherein the water soluble metal salt is a water soluble inorganic metal salt.

27. The process according to claim 26, wherein the water soluble metal salt is selected from the group consisting of aluminum sulfate, potassium aluminum sulfate, lithium dihydrogen phosphate, sodium dihydrogen phosphate, potassium trisulfite, potassium hydrogen sulfate, potassium dihydrogen phosphate, sodium hydrogen sulfite, calcium aluminum sulfate, and combinations thereof.

28. The process according to claim 1, wherein the process further comprises
   (c) cooling the biphasic mixture after the concentrating step.

* * * * *